(12) United States Patent
Bao et al.

(10) Patent No.: US 6,589,629 B1
(45) Date of Patent: Jul. 8, 2003

(54) PROCESS FOR FABRICATING PATTERNED, FUNCTIONALIZED PARTICLES AND ARTICLE FORMED FROM PARTICLES

(75) Inventors: Zhenan Bao, North Plainfield, NJ (US); Edwin Arthur Chandross, Murray Hill, NJ (US); Xiaochen Linda Chen, Wappingers Falls, NY (US); John A. Rogers, New Providence, NJ (US); Marcus Weldon, Summit, NJ (US)

(73) Assignee: Lucent Technologies Inc., Murray Hill, NJ (US)

( * ) Notice: Subject to any disclaimer, the term of this patent is extended or adjusted under 35 U.S.C. 154(b) by 161 days.

(21) Appl. No.: 09/659,550

(22) Filed: Sep. 11, 2000

(51) Int. Cl.[7] .............................. B32B 5/16; C25D 5/02
(52) U.S. Cl. ...................... 428/144; 205/118; 205/221; 205/223; 427/201; 427/203; 427/205; 427/215; 427/261; 427/271; 428/323; 428/403
(58) Field of Search ........................... 205/85, 109, 118, 205/128, 221, 223; 427/201, 203, 205, 215, 261, 271; 428/323, 403

(56) References Cited

U.S. PATENT DOCUMENTS

| | | | |
|---|---|---|---|
| 4,661,408 A | | 4/1987 | Lau et al. |
| 5,081,160 A | | 1/1992 | Strom et al. |
| 5,172,267 A | | 12/1992 | Yablonovitch |
| 5,324,752 A | | 6/1994 | Barretto et al. |
| 5,460,831 A | | 10/1995 | Kossovsky et al. |
| 5,532,279 A | | 7/1996 | Barretto et al. |
| 5,582,955 A | * | 12/1996 | Keana et al. ............... 430/296 |
| 5,600,483 A | | 2/1997 | Fan et al. |
| 5,747,256 A | | 5/1998 | Yan et al. |
| 5,763,768 A | | 6/1998 | Henderson et al. |
| 5,962,228 A | | 10/1999 | Brenner |
| 6,103,868 A | * | 8/2000 | Heath et al. ............... 528/482 |
| 6,133,047 A | * | 10/2000 | Elaissari et al. ............ 436/526 |
| 6,369,206 B1 | * | 4/2002 | Leone et al. ............. 530/391.5 |
| 6,423,551 B1 | * | 7/2002 | Weiss et al. ................ 436/518 |

OTHER PUBLICATIONS

P.S.J. Russell, "Photonic Band Gaps," *Physics World*, 37, (1992).
I. Amato, "Designing Crystals That Say No To Photons," *Science*, vol. 255, 1512 (1993).
J.G. Fleming et al., "Three–dimensional photonic crystal with a stop band from 1.35 to 1.95 $\mu$m," *Optics Letters*, vol. 24, 49–51 (1999).
B.H. Cumpston et al., "Two–photon polymerization initiators for three–dimensional optical data storage and microfabrication," *Nature*, vol. 398, 51–54 (1999).
B.T. Holland et al., "Synthesis of Macroporous Minerals with Highly Ordered Three–Dimensional Arrays of Spheroidal Voids", *Science*, vol. 281, 538 (1998).
E.G. Judith et al., Preparation of Photonic Crystals Made of Air Spheres in Titania, *Science*, vol. 281, 802 (1998).
A.A. Zakhidov et al., "Carbon Structures with Three–Dimensional Periodicity at Optical Wavelengths," *Science*, vol. 282, 897 (1998).
Y. Xia et al., "Soft Lithography," *Agnew. Chem. Int. Ed.*, vol. 37, 550–575 (1998).

(List continued on next page.)

Primary Examiner—H. Thi Le

(57) ABSTRACT

A technique for forming functionalized particles, where such particles are readily formed into periodic structures. A layer of particles is formed on a substrate, a first material is deposited over at least a portion of each of the particles, and then a functionalizing agent is attached to the first material. The functionalized particles are then capable of being formed into an ordered structure, by selection of appropriate complementary functionalizing agents on a substrate and/or on other particles and/or on other regions of the same particles.

29 Claims, 7 Drawing Sheets

OTHER PUBLICATIONS

A. Ulman, *Ultrathin Organic Films*, Academic Press, 237–301 (1999).

A.F. Bettleheimd et al., *Introduction to General Organic Biochemistry*, 4th Ed., Harcourt Brace College Publishers.

L.H. Dubois et al., "Molecular Ordering of Organic Sulfur Compounds on Au(111) and Au(100)–Adsorption from Solution and in Ultrahigh Vacuum," *J. Chem. Phys.*, vol. 98, 678–688 (1993).

R. Levicky et al., "Using self–assembly to control the structure of DNA monolayers on gold: A neutron reflectivity study," *J. Am. Chem. Soc.*, vol. 120, 9787–9792 (1998).

A. van Blaaderen et al., "Template–directed colloidal crystallization" *Nature*, vol. 385, 321 (1997).

S.A. Johnson, et al., "Ordered Mesoporous Polymers of Tunable Pore Size from Colloidal Silica Templates", *Science*, vol. 283, 963 (1999).

S.H. Park, et al., "Macroporous Membranes with Highly Ordered and Three–Dimensionally Interconnected Spherical Pores", *Adv. Mater.* 10, No. 13, p. 1045 (1998).

H–B. Sun, et al., "Three–dimensional photonic crystal structures achieved with two–photon–absorption photopolymerization of resin", *Applied Physics Letters*, vol. 74, No. 6, (1999).

U.S. patent application Ser. No. 09/248858 filed on Feb. 11, 1999.

U.S. patent application Ser. No. 09/248577 filed on Feb. 11, 1999.

U.S. patent application Ser. No. 09/312165 filed on May 14, 1999.

* cited by examiner

PROCESS FOR FABRICATING PATTERNED, FUNCTIONALIZED PARTICLES AND ARTICLE FORMED FROM PARTICLES

BACKGROUND OF THE INVENTION

1. Field of the Invention

The invention relates to fabrication of functionalized particles useful for forming a variety of ordered, periodic structures.

2. Discussion of the Related Art

There is an increasing interest in periodic two- and three-dimensional structures, for a variety of applications, including photonics, filters, catalysts, and biocompatible materials. Of particular interest for photonics applications are periodic dielectric structures, also referred to as photonic crystals (PCs), particularly PCs exhibiting gaps in photonic band structures. Such photonic band gap (PBG) materials are discussed, for example, in P. S. J. Russell, "Photonic Band Gaps," *Physics World*, 37, August 1992; I. Amato "Designing Crystals That Say No to Photons," *Science, Vol.* 255, 1512 (1993); J. G. Fleming and S. Y. Lin, "Three-dimensional photonic crystal with a stop band from 1.35 to 1.95 $\mu$m," *Optics Letters*, Vol. 24, 49–51 (1999); B. H. Cumpston et al., "Two-photon polymerization initiators for three-dimensional optical data storage and microfabrication," *Nature, Vol.* 398, 51–54 (1999); and U.S. Pat. Nos. 5,600,483 and 5,172,267.

PBG materials exhibit a photonic band gap, analogous to a semiconductor's electronic band gap, that suppress propagation of certain frequencies of light, thereby offering, for example, photon localization or inhibition of spontaneous emissions. Such structures are potentially useful as waveguides and microcavities for lasers, filters, polarizers, and planar antenna substrates. A PBG material is generally formed by combining a high refractive index dielectric material with a three-dimensional lattice of another material (or a lattice of cavities or voids) having a low refractive index, to form a three-dimensional Bragg grating. The propagation of light in the PBG structure therefore depends critically on the particular energy of the photon; photons having energy within the PBG are unable to propagate through the material, and are consequently rejected (reflected).

The photonic band structure depends on the precise details of the physical structure and on its refractive index contrast, and some difficulty has arisen in fabricating such materials. Specifically, it has been difficult to organize an extended three-dimensional periodic lattice with submicron and micron scale index contrast, particularly with high refractive index materials. (Periodicities on a submicron and micron scale, as used herein, indicate that a structure contains repeating units, the repetition occurring at a distance falling within the range 0.1 $\mu$m to 100 $\mu$m.)

In one approach, reflected in the above-cited references, solid materials are provided with numerous holes by mechanical techniques such as drilling, by lithographic techniques such as etching, or by selective polymerization. These approaches have provided useful results, but are limited by the ability of current processing technology to provide the necessary structure, e.g., they tend to be complicated and are only applicable to a limited number of materials and structures.

In another approach, ordered colloidal suspensions or sediments, e.g., from particles of soluble, etchable, chemically distinguishable, and relatively low refractive index materials such as polystyrene, referred to as colloidal crystals, are used as templates for infiltration or deposition of high refractive index materials in a desired structure, and the particles are then etched away or. burned out to provide the voids. See e.g., B. T. Holland et al., "Synthesis of Macroporous Minerals with Highly Ordered Three-Dimensional Arrays of Spheroidal Voids," *Science,* Vol. 281, 538 (1998); E. G. Judith et al., "Preparation of Photonic Crystals Made of Air Spheres in Titania," *Science,* Vol. 281, 802 (1998); and A. A. Zakhidov et al., "Carbon Structures with Three-Dimensional Periodicity at Optical Wavelengths," *Science,* Vol. 282, 897 (1998). The infiltration/deposition has been performed, for example, by an alkoxide sol-gel technique and by chemical vapor deposition (CVD). The results attained by these methods have been interesting, but are far from providing a commercially feasible product. In particular, formation of a colloidal crystal having the desired order and periodicity over extended distances has been difficult, and thus the resulting structures often lack the requisite order for photonics applications.

Improvements in fabricating periodic three-dimensional structures are reflected in co-assigned patent applications Ser. Nos. 09/248,858, 09/248,577, and 09/312,165 (our reference, respectively, Braun 1-18-4, Braun 2-9-5, and Braun 3-6). However, techniques that provide even more improved fabrication of such structures would be desirable.

SUMMARY OF THE INVENTION

The invention provides a technique for forming functionalized particles, where such particles are readily formed into ordered, periodic structures. According to the invention, a layer of particles is formed on a substrate, a first material is deposited over at least a portion of each of the particles, and then a functionalizing agent is attached to the first material. (Functionalizing agent indicates a material capable of self-assembly to or capable of being bound to a complementary agent or material, thereby allowing control over the arrangement of functionalized particles into a desired structure. Attached indicates, for example, chemical binding, chemisorption, or even attraction.) The functionalized particles are capable of being formed into an ordered structure, by selection of appropriate complementary functionalizing agents on a substrate and/or on other particles and/or on other regions of the same particles.

In one embodiment, a portion of the first material is removed from the particle prior to functionalization to provide a selected region to which the functionalizing agent will attach, e.g., the first material is a metal deposited by electron beam evaporation, and a wet etch is performed to remove part of the deposited metal. See, e.g., FIGS 1A–1C. (Material, as used herein, indicates one or more materials deposited simultaneously or sequentially, e.g., a metal alloy or sequential deposition of two different materials.)

In another embodiment, reflected in FIGS. 3A–3D, prior to depositing the first material, a removable layer is formed over the layer of particles such that portions of the particles are exposed above the removable layer. The coverage of the first material is thereby able to be controlled by the extent to which the particles are exposed. The first material is deposited onto the exposed portions, and the removable layer is removed—typically before attaching the functionalizing agent.

It is possible to functionalize more than one region on the particles. For example, in an embodiment reflected in FIGS.

6A–6D, to add an additional functionalized site, the functionalizing agent of the functionalized particles is attracted onto the surface of a substrate to form a layer of the functionalized particles. Then, a removable layer is formed such that non-functionalized portions of the particles are exposed above the removable layer. A second material, which can be different from the first material, is formed on at least part of the non-functionalized exposed portions. A second functionalizing agent, which can be different from the first functionalizing agent, is attached to the second material, and the removable layer is then removed—typically before attaching the second functionalizing agent. Additional functionalization is also possible.

In one approach, suitable for a variety of embodiments, the particles are silica spheres, the first material consists of a layer of gold on titanium, and the functionalizing agent is a single strand DNA having a thiol end group that attaches, i.e., chemically binds in this case, onto the gold. The complementary single strand DNA is then able to be used to order the particles in a desired manner.

The functionalized particles are capable of being assembled in a variety of ways, to form a variety of structures, using principles of self-assembly.

DETAILED DESCRIPTION OF THE INVENTION

The invention provides a technique for functionalizing particles, such that the particles are capable of being formed into two- or three-dimensional structures. Typically, the particles are spheres, although a variety of shapes are possible. (Spheres are used herein to illustrate the invention, but the techniques applied to spheres are similarly applicable to such other shapes.)

The first step in functionalizing the particles is generally to form a single layer of the particles on a substrate, e.g., by spin coating, solution casting, or doctor blading a dispersion of the particles. A silicon wafer, e.g., a single crystal (100) oriented wafer, is generally useful, although a variety of substrates are possible, including both flat and textured substrates.

Figure 1A:
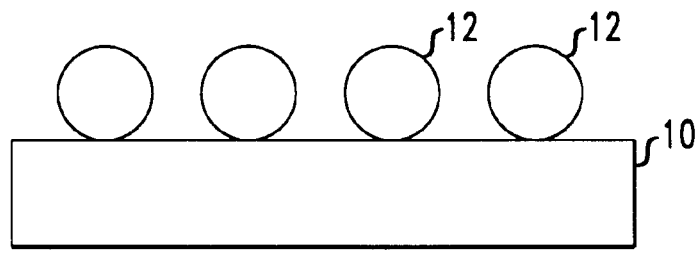
FIGS. 1A–1C illustrate one embodiment of the invention.
Figure 1B:
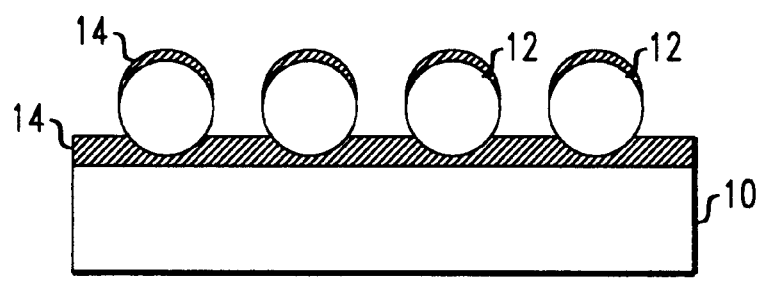
Figure 1C:
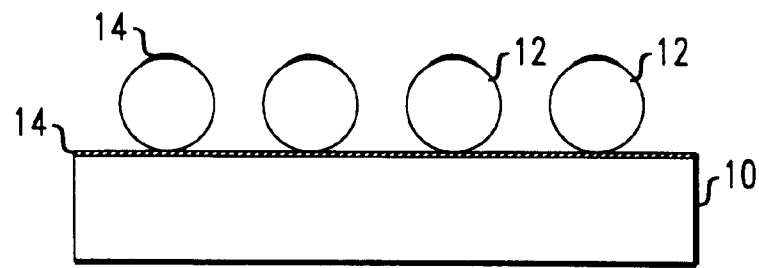

Once the particle monolayer is formed, there are several approaches to functionalizing the particles. In one approach, reflected in FIGS. 1A to 1C, there is provided a substrate 10 with a monolayer of spheres 12 formed thereon. A first material 14 is deposited onto the particles 12, generally so that the material 14 covers only a portion of the particles 12, as shown in FIG. 1B. An etch is then performed to leave a desired amount of the first material 14 on the particles 12, as shown in FIG. 1C. Generally, the substrate and particles are then exposed to a solution containing functionalizing agent that attaches to the first material. (Etch includes, for example, exposure to etchant materials, exposure to an etching process, e.g., a plasma etch, as well as any other process that removes the first material, e.g., application of heat.)

Figure 2A:
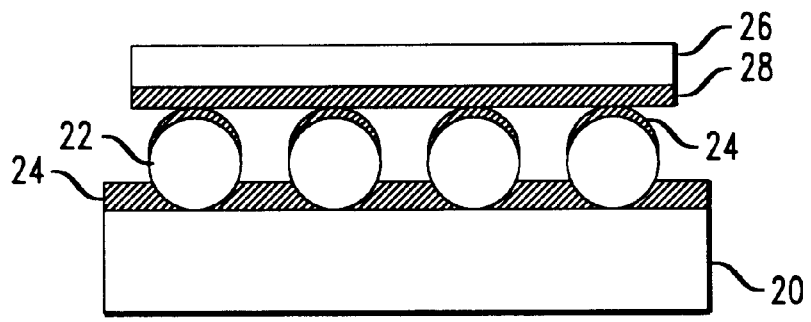
FIGS. 2A–C illustrate another embodiment of the invention.
Figure 2B:
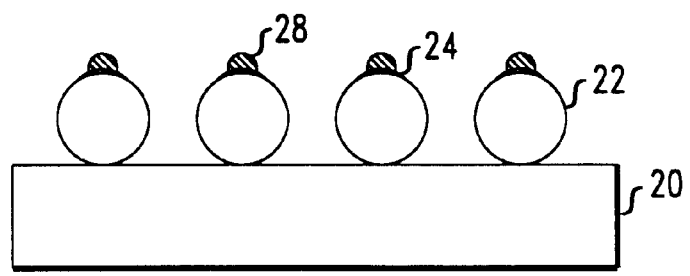
Figure 2C:
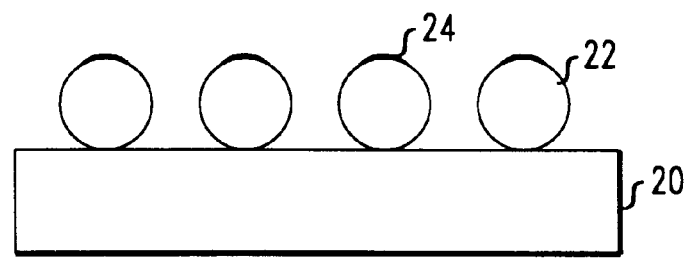

A modification to this first approach is reflected in FIGS. 2A to 2C. A substrate 20 having particles 22 on which a first material 24 has been formed is provided. A stamp 26, e.g., a polydimethylsiloxane stamp, having protecting groups 28 attached (in this case absorbed) thereto is stamped onto the first material 24, such that the protecting groups 28 are transferred onto the first material 24, as shown in FIG. 2B. Such stamping techniques are known in the art, as discussed, for example, in Y. Xi and G. M. Whitesides, "Soft Lithography," *Angew. Chem. Int. Ed.,* Vol. 37, 550–575 (1998). Upon etching to remove a portion of the deposited first material 24, the protecting groups 28 provide improved control (when selected to be substantially inert to the particular etching technique). Specifically, the presence of the protecting groups impedes removal of the portion of the first material 24 to which the protecting groups 28 are attached. (Protecting groups indicate any material that provides at least partial protection from an etch of the first material.) A subsequent etch is then typically performed to remove the protecting groups 28, while leaving the first material 24 substantially intact. This technique, by using the protecting groups, requires less stringent control over the etch of the first material. In an advantageous embodiment, the first material consists of a layer of gold on titanium, and the protecting groups are an alkanethiol compound. A conventional wet etchant, as reflected in the examples, is capable of removing the gold (possibly with at least a portion of the titanium), and an oxygen plasma etch is useful for removing the alkanethiol while leaving the gold/titanium substantially intact.

Figure 3A:
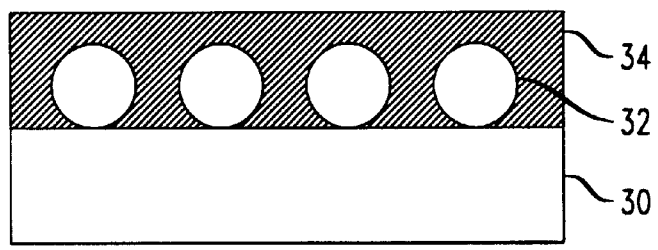
FIGS. 3A–3D illustrate a further embodiment of the invention.
Figure 3B:
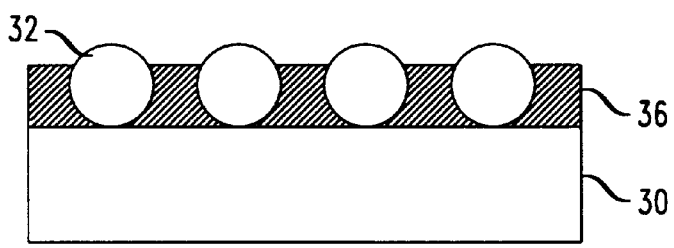
Figure 3C:
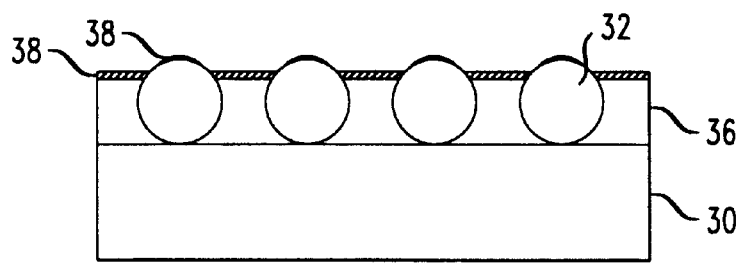
Figure 3D:
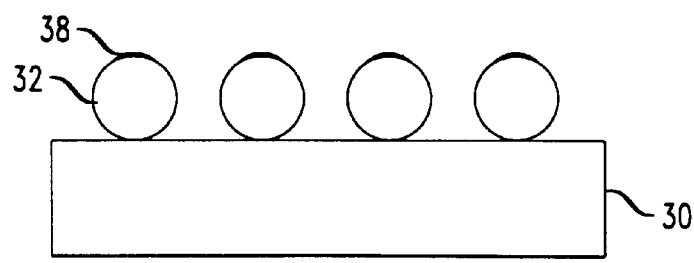

An alternative approach uses a removable layer to control the deposition of the first material on the particles, as reflected in FIGS. 3A to 3D. This approach starts with a monolayer of spheres 32 on a substrate 30. An initial removable layer 34, e.g., a conventional photoresist, is then formed over the particles 32, as shown in FIG. 3A. It is possible to form the initial removable layer by conventional techniques, e.g., spin-coating. As shown in FIG. 3B, the initial removable layer 34 is then treated to provide a removable layer 36 that exposes a portion of the particles 32. Reactive ion etching is a useful technique for providing this exposure. (It is also possible to directly form the removable layer such that portions of the particles are exposed.) A first material 38 is then deposited onto the particles 32 and the removable layer 36, with the extent of coverage at least partially controlled by the extent of exposure of the particles 32, as shown in FIG. 3C. The removable layer 36 is then removed, e.g., dissolved by acetone in the case of a typical photoresist, to provide the particles 32 having the desired coverage of the first material 38 formed thereon, as shown in FIG. 3D. The same materials and techniques presented in the above embodiments are similarly useful with this approach.

In addition to these particular approaches to providing a first material onto particles, modifications and combinations of these approaches are also possible.

It is possible to use particles formed from a variety of materials, including inorganics (e.g., oxides such as silica), polymers, and metals. Spheres are typically suitable. The average diameter of the spheres generally ranges from 10 to 1000 $\mu$m, more typically 50 nm to 100 $\mu$m. Where other shapes are used, the shapes generally have an effective diameter within the same size range. (Effective diameter indicates the diameter of a sphere having the equivalent volume of the particle.) The size of the particles, however, is capable of being widely varied depending on the intended use of the functionalized particles. Advantageously, the particles have a high size uniformity, in order to attain relatively uniform functionalization, e.g., when the particles are formed into a monolayer on a substrate, there will be little height variation. For example, the diameter of individual spheres advantageously does not vary more than 5% from the average diameter.

The first material is any material suitable for deposition onto the particles and for subsequent functionalization. Suitable materials capable of coupling to a variety of end groups are known. See, e.g., A. Ulman, *Ultrathin Organic Films*, Academic Press, 1999, 237–301. For example, both thiols and disulfides are known to bind to gold, thiols are known to bind to silver, nickel, copper, and platinum, isocyanide groups are known to bind to platinum, and carboxylic acid groups are known to bind to metal oxides. Other ligands, e.g., phosphines, phosphonates, and amines, also tend to interact with metals. The material is deposited by any suitable technique. Typically, a chemical vapor deposition or physical vapor deposition technique is used with metals, e.g., sputtering or electron beam evaporation. Advantageously, where a subsequent etch of the first material is intended, the material is deposited in a thickness gradient, e.g., by use of a collimated beam of material, such that the etch removes the thinner regions while leaving some material on the thicker regions.

Figure 4:
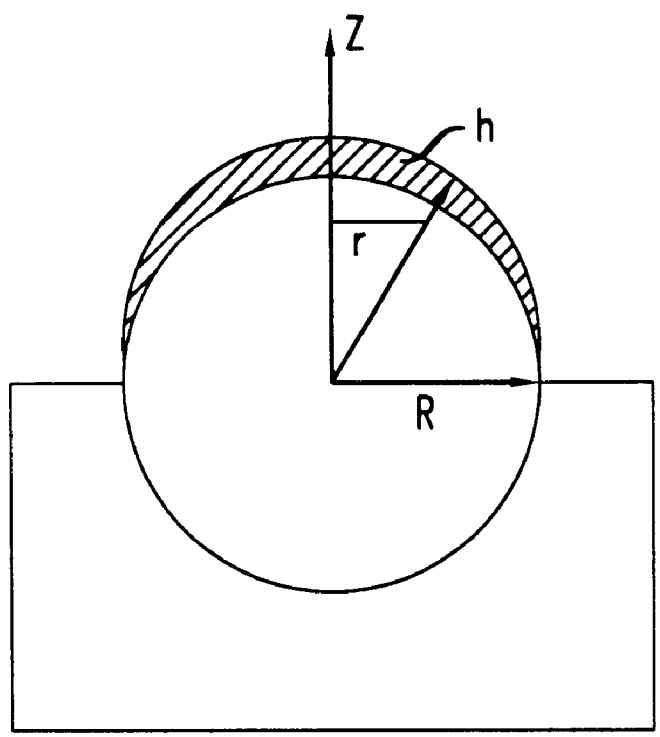
FIG. 4 illustrates the use of metal caps of non-uniform thickness, according to an embodiment of the invention.

For example, sequential electron beam evaporation of metal onto silica spheres leaves the spheres with about half their surface covered with metal, as reflected in FIG. 4. The metal thickness h at any point on the sphere as a function of the distance r from that point to the z-axis can be expressed as:

$$h(r)=H_0[1-(r/R)^2]^{1/2}$$

where $H_0$ is the evaporated metal thickness for a planar wafer, and R is the radius of the sphere. (The equation assumes that the metal source is a plane source—not a point source, and that $H_0<<R$.) When r is zero, h reaches its maximum $H_0$, and when r equals R, the thickness of the metal layer is zero. Because of the non-uniformity of the thickness, control of the size of the metal cap is possible by performing an etch sufficient to remove the areas of lower thicknesses.

The etchant selected to remove a portion of the first material depends on the particular material. Wet etchants capable of etching a variety of materials are known in the art. Dry etching techniques are sinmilarly well-known. A high level of control of the etchant is necessary in some embodiments to attain the desired coverage on the particle, e.g., where a removable layer is not used.

Use of a removable layer generally avoids the need for etching of the first material, and thus tends to allow better control over the process. Thinner layers of the first material are generally able to be formed, since no etch is required. The thinner layers also promote easier removal of the removable layer. The removable layer is typically a photoresist, and techniques for depositing and removing such photoresists are well known. It is also possible to use other materials that provide a similar function.

In an advantageous embodiment, the spheres are silica, and the first material consists of a layer of gold on titanium.

Where etching is required, the etchant for the gold is typically a conventional wet etch used in semiconductor fabrication. (RVile such an etchant is designed to primarily remove the gold, some titanium tends to be etched away as well.) One such etching solution is a basic solution prepared by dissolving 16.8 g KOH, 1 g $K_3Fe(CN)_6$, 0.13 g $K_4Fe(CN)_6$, 7.4 g $Na_2S_2O_3$ in 300 mL water. The etching rate of gold is about 0.7 Å per second at 25° C. The solution is stable for at least 2 hours. An alternative—and more conventional—etching solution, which is acidic, is a Gold Etchant type TFA (Transene Comp. Inc., Danvers, Mass.). In its undiluted form, the TFA has etching rate about 28 Å of Au per second at 25° C. A useful water:etchant ratio for a diluted form is 4:1, in order to provide better control over etching, i.e., to slow the etching rate to a time period more reasonable for practical applications.

It is also possible to attach the functionalizing agent directly to the particle. This is typically performed by use of a removable layer. The functionalizing agent would otherwise be expected to attach to the entire surface of the particle, whereas selective functionalization is generally desired. In one such embodiment, the spheres are silica and the first material is a silane compound, e.g., a silane compound having an attached $NH_2$ group. Optionally, the compound is converted to an ammonium ion that makes it possible to use electrostatic attraction to form an ordered structure from the resultant particles, e.g., by using a substrate or additional particles having an opposite charge. A variety of other chemical and physical reactions are also capable of providing a first material that constitutes the functionalizing agent, e.g., metal particles with appropriate coupling groups such as the combinations listed above.

When a first material is present, the particles having the first material thereon are exposed to a functionalizing agent that attaches to the first material. Typically, exposure to a solution containing the functionalizing agent is sufficient to provide the attachment. An example of a first material/ functionalizing agent combination is gold and thiol-terminated single-strand DNA (referred to herein as HS-ssDNA). The single strand is capable of forming a helix with its complementary strand (HS-ssDNA-c), and the complementary strand is thus often attached to a substrate, to other particles, or to other locations on the same particle. It is also possible to attach groups onto the first material that provide a particular chemical reaction, charge interaction, or biological interaction with another group capable of being put onto a substrate, onto other particles or onto other locations on the same particle. It is possible to functionalize different regions of particles with groups that are attracted, e.g., bind, to one another (i.e., complementary groups) or with groups that are substantially inert to one another, such that the particles organize themselves in a desired manner.

Formation of a double helix between a single DNA chain and its complementary strand is well known. Each strand contains a specific sequence of recognition groups, called bases, abbreviated as A, T, C, and G, and there is a specific complementary relationship between the bases: A only binds to T and G only binds to C. (See, e.g., A. F. Bettleheimd and J. March, *Introduction to General Organic Biochemistq*, $4^{th}$ Ed., Harcourt Brace College Publishers.).The adsorbed ssDNA binds covalently to the gold through the thiol end groups, as well as through nonspecific (i.e., other than through the thiol group) interactions with the gold. These nonspecific interactions are generally undesirable, in that they reduce the precision of the particle functionalization. To reduce or avoid the nonspecific interactions, it is possible to treat the adsorbed ssDNA with a compound such as mercaptohexanol—a small organic molecule that also attaches to gold through a thiol group. The mercaptohexanol forms a self-assembled monolayer that displaces the nonspecific interactions between the ssDNA and the gold, thereby providing a ssDNA layer in which substantially all the strands are attached to the gold only by way of the thiol end groups. The mercaptohexanol monolayer possesses a hydroxyl (HO−) terminated top surface, to which the HS-ssDNA does not strongly adsorb. A suitable treatment with the mercaptohexanol involves immersion of the particles in a 1 mM aqueous solution of mercaptohexanol (MCH) for 5 minutes, followed by thorough rinsing. The thiol group on the MCH chemically adsorbs to any uncovered gold surface, creating a mixed monolayer of ssDNA/MCH.

The DNA is optionally selected according to known methods, such as R. Levicky et al., "Using self-assembly to control the structure of DNA monolayers on gold: A neutron reflectivity study," *JACS*, Vol. 120, 9787–9792 (1998). The DNA is advantageously a 25-base oligonucleotide with the following sequence: 5'-HS-$(CH_2)_6$-CAC GAC GTT GTA AAA CGA CGG CCA G-3'. (This thiolated single strand DNA is commercially available, e.g., from Research Genetics of Huntsville, Ala..) The complementary single-stranded DNA is a second 25-mer with the following sequence: 5'-HS-$(CH_2)_6$-CTG GCC GTC GTT TTA CAA CGT CGT G-3'. Larger DNA strands having more bases will tend to facilitate self-assembly and provide improved results with relatively large spheres, e.g., spheres >10 μm.

It is possible to obtain HS-ssDNA and its complementary DNA HS-ssDNA-c with the thiol groups in their protected disulfide forms. Before adsorption onto a first material, the disulfides must be reduced. This reduction of disulfides is optionally carried out by mixing 10 equiv. of tris-(2-carboxyethyl)phosphine (TCEP) with 1.0 equiv. of 1.0 μM DNA in 1.0 M $KH_2PO_4$ buffer solution (pH 6.7) for 10 min. It is then possible for the attachment of the HS-ssDNA to proceed onto particles having an appropriate first material, e.g., gold, by placing the particles in this solution for about 120 min. After adsorption, the substrate is preferably rinsed thoroughly with deionized water. The assembly of HS-ssDNA-C on Au patterned substrates is optionally carried out by placing Au patterned substrates in 1.4 μM DNA (pH 7.0) in trisethylenediaminetetraacetic acid-1 M NaCl buffer for about 120 min. After adsorption, the substrate is typically rinsed thoroughly with deionized water.

A useful group for providing a variety of functionalizing end groups on particles is a long chain alkanethiol molecule such as $(HS(CH_2)_nX)$, where n is 1 to 20, typically 8 to 20. Such molecules are capable of being adsorbed onto gold surfaces through the thiol headgroup (—SH) to form densely-packed, robust, often crystalline monolayer films. (See, e.g., L. H. Dubois et al., "Molecular Ordering of Organic Sulfur Compounds on Au(111) and Au(100)-Adsorption from Solution and in Ultrahigh Vacuum," *J. Chem. Phys.*, Vol. 98, 678–688 (1993).) The surface chemical and physical properties of the monolayer films are capable of being controlled by varying the functional end group (X) of the alkanethiol molecule. It is possible for this terminal functionality to be a single strand DNA, as discussed above, but other groups are also possible, such as a primary or secondary amine capable of forming a chemical bond with complementary groups.

Figure 5A:
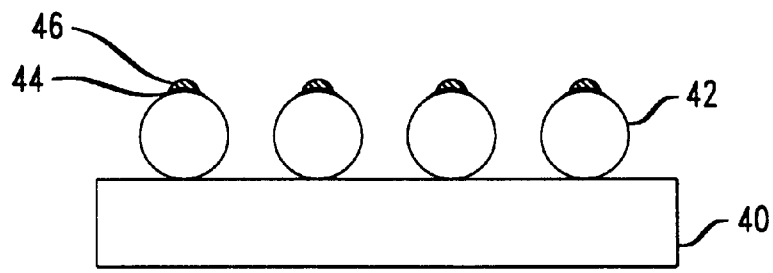
FIGS. 5A–5C illustrate a technique for functionalizing and assembling particles of the invention.
Figure 5B:
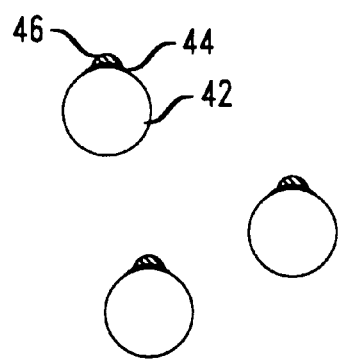
Figure 5C:
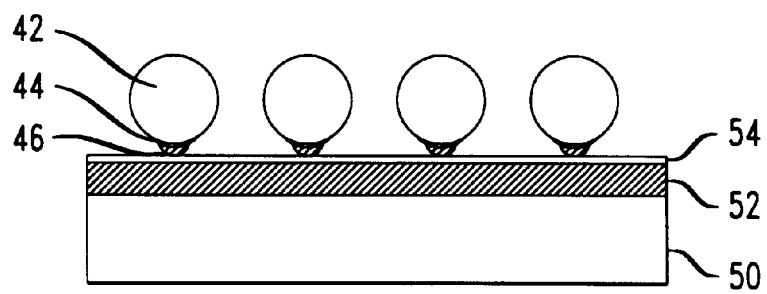

FIGS. 5A to 5C illustrate the general technique for organizing the particles by use of the functionalizing agent. FIG. 5A shows a monolayer of particles 42 on a substrate 40. The particles have a first material 44 and a functionalizing agent 46, provided according to, e.g., one of the above embodiments. The particles are removed from the substrate, e.g., by sonication in solution, as shown in FIG. 5B. As shown in FIG. 5C, another substrate 50 is provided. The substrate 50 has a surface layer 52 to which is attached functionalizing agent 54, the functional agent 54 being complementary to the functionalizing agent 46 located on the particles 42. Upon placing substrate 50 into a solution containing the particles 42, the functional agent 46 is attracted to the complementary functional agent 54 on the surface of the substrate, and thereby forms a monolayer on the substrate. As discussed below, this monolayer allows subsequent functionalization of other regions of the particles, or subsequent formation of additional layer, or, where a 2-D structure is desired, subsequent steps leading to the desired structure.

Figure 6A:
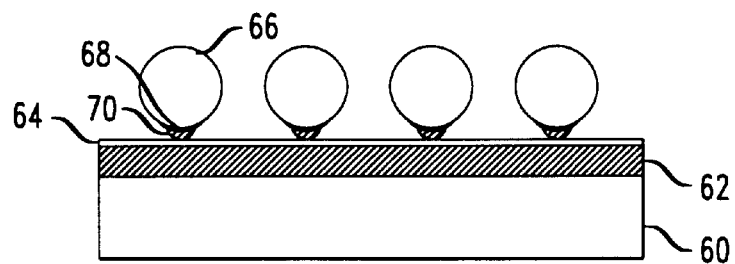
FIGS. 6A–6D illustrate a technique for functionalizing a second site of particles according to the invention.
Figure 6B:
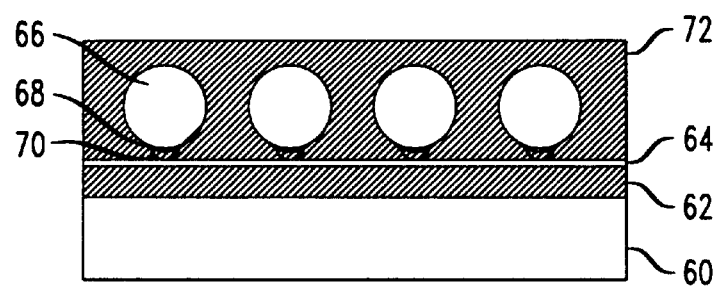
Figure 6C:
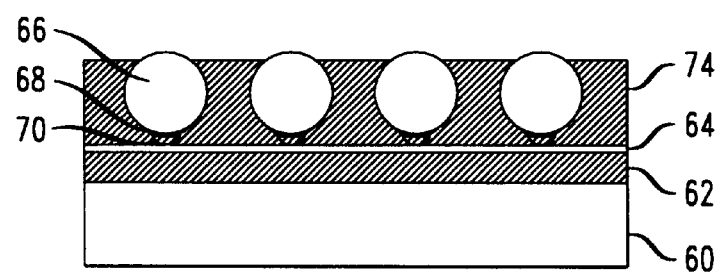
Figure 6D:
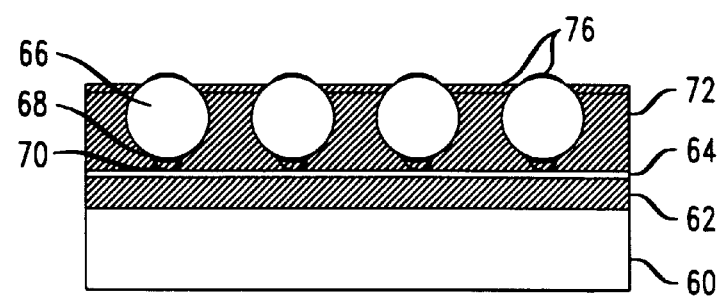

More than one region of an individual particle is capable of being functionalized, using, for example, the above techniques. FIGS. 6A–6D illustrate one method for providing multiple functionalization. FIG. 6A shows particles 66 having a first material 68 and a functionalizing agent 70. The substrate 60 has a surface layer 62 to which is attached a functionalizing agent 64, which is complementary to the functionalizing agent 70 of the particles 66. The particles 66 are thus attracted to the surface of the substrate 60. As shown in FIGS. 6B to 6C, an initial removable layer 72 is formed over the particles 66, and then etched to provide a removable layer 74 above which a portion of the particles 66 are exposed. As shown in FIG. 6D, a first material 76 is formed onto at least part of the exposed portion, and then functionalization can be performed as described above.

Figure 7A:
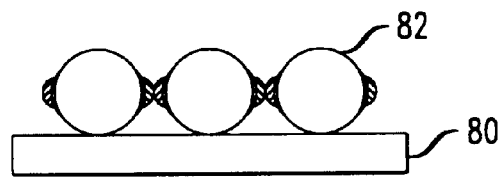
FIGS. 7A–7D illustrate a technique for functionalizing a third site of particles according to the invention.
Figure 7B:
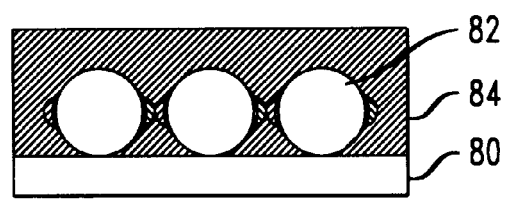
Figure 7C:
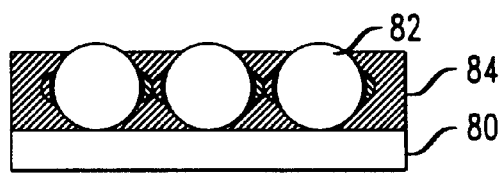
Figure 7D:
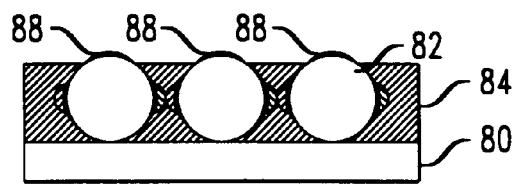

Additional regions are capable of being functionalized in a similar manner. For example, FIG. 7A shows a chain 82 of particles having dualfunctionalization. A monolayer of the chain 82 is formed onto a substrate 80. As shown in FIGS. 7B and 7C, an initial removable layer 84 is formed over the chain 82, and then etched down to a removable layer 86 above which a portion of the chain 82 is exposed. As shown in FIG. 7D, a first material 88 is then formed on at least a part of the exposed portions of the particles of the chain 82, and functionalization is thereby possible as described above. Further functionalization is possible according to these and similar techniques.

Once the functionalized particles are formed, there are numerous ways to provide for self-assembly of desired structures. For example, it is possible to form spheres having a functionalizing agent at one region and the complementary agent at the opposite side of the sphere, such that parallel chains of the spheres will form from an appropriately patterned substrate.

It is also possible, for example, to form two types of spheres—the first type having a first functionalizing agent located at two regions about 180° from each other, and the second type having a second functionalizing agent—complementary to the first functionalizing agent—also located at two regions about 180° from each other. It is then possible to form a monolayer of the first type on an appropriately patterned substrate from a solution of the first type of spheres, and then expose the monolayer to. a solution of the second type to form a single layer thereon. The process is then alternated between the first type and the second type of spheres, until the desired structure is formed.

It is also possible, for example, to form spheres having a functionalzing agent at two regions about 180° from each other. The spheres are mixed with molecules having two end groups complementary to the functionalizing agent. From an appropriately patterned substrate, parallel chains of alternating spheres and molecules are grown.

The invention will be further clarified by the following examples, which are intended to be exemplary.

EXAMPLE 1

A colloidal solution containing 1 µm $SiO_2$ spheres was formed as follows. In a 20 mL glass. bottle were mixed 1 g of a 2 wt. % solution of nominally 1 µm $SiO_2$ spheres in water (obtained from Duke Scientific), 9 g of methanol, 0.3 g of surfactant FC-430 (obtained from 3M Corporation), 10 to 20 drops (about 0.5 to 1 mL) of N,N-dimethylformamide (DMF) and 25 drops (about 1 mL) of $NH_4OH$ (28 wt. % $NH_3$ in water). The solution was sonicated for 5 minutes to provide homogeneous mixing.

A single-crystal (100) silicon wafer was used as the substrate for supporting the $SiO_2$ spheres. The wafer was cleaned by sequential washing with acetone, isopropanol and deionized water. The colloidal solution was spin-coated on the silicon wafer by spreading at 75 rpm for 5 seconds, spinning at 1000 rpm for 40 seconds, and heating the substrate at 120° C. for about five minutes to promote removal of all solvents. The coverage of the spheres on wafer was between 5 and 90% of the surface. Remaining surfactant was removed by placing the substrate under $O_2$ plasma (50 W, 0.31 Torr) for about 5 minutes.

Electron-beam evaporation was used to deposit a titanium layer about 15 Å thick followed by a gold layer about 200 Å thick, as measured at the top of the sphere. Deposition onto the spheres occurred nonuniformly, as would be expected with a collimated beam, with the tops of the spheres (i.e., the region furthest from the substrate surface) having the highest thickness, the edges of the spheres having a decreasing thickness, and the bottom half of the spheres having substantially no metal formed thereon.

A 2 to 3 minute etch was performed with a basic solution prepared by dissolving 16.8 g KOH, 1 g $K_3Fe(CN)_6$, 0.13 g $K_4Fe(CN)_6$, 7.4 g $Na_2S_2O_3$ in 300 mL water.

HS-ssDNA and its complementary HS-ssDNA-c, of the type discussed above, were obtained in their protected disulfide forms, and the disulfides were reduced as detailed above. The particles were then placed in the reducing solution for about 120 min. After adsorption, the substrate was rinsed thoroughly with deionized water. The assembly of HS-ssDNA-c on gold-patterned substrates was performed by placing the gold-patterned substrates in 1.4 µM DNA (pH 7.0) in trisethylenediaminetetraacetic acid-1 M NaCl buffer for about 120 min. After adsorption, the substrate was rinsed thoroughly with deionized water. The patterned substrates were immersed in 1 mM aqueous solution of 6-mercaptohexanol (MCH) for 5 minutes and then thoroughly rinsed. The thiol group on the MCH adsorbed to any remaining uncovered gold surface, creating a mixed monolayer of HS-ssDNA-c/MCH or HS-ssDNA/MCH.

EXAMPLE 2

A monolayer of silica spheres was formed on a silica wafer as in Example 1. The wafer was held at 200° C. for 15 minutes to remove residual water and promote adhesion between the spheres and the substrate. A Novolac-type photoresist (AZ5214 obtained from Clariant Corp., Somerville, N.J.) was spin coated onto the spheres by spreading at 75 rpm for 5 seconds, spinning at 3000 rpm for 40 seconds, and baking at 120° C. for 90 seconds to remove the solvent present in the photoresist. The result was a smooth photoresist film about 1.6 µm thick. An oxygen plasma at 50 mW and 0.311 Torr was used to etch the photoresist layer for about 5 minutes, down to a thickness of about 950 nm, thereby exposing the top portions of the silica spheres. Then, 20 Å of titanium followed by 50 Å of gold, as measured at the top of the sphere, were deposited on the exposed portions of the spheres by electron-beam evaporation. The photoresist was then removed by exposure to acetone. The relatively thin metal layers allowed relatively easy removal of the photoresist. The spheres were then functionalized as in Example 1.

Other embodiments of the invention will be apparent to those skilled in the art from consideration of the specification and practice of the invention disclosed herein.

What is claimed is:

1. A process for fabricating functionalized particles, comprising the steps of:
    forming a layer of particles on a substrate;
    depositing a first material over a selected portion of each of the particles thus forming a periodic structure with regions of first material and regions without first material; and
    attaching a functionalizing agent to the first material.

2. The process of claim 1, wherein the first material comprises gold and wherein the functionalizing agent comprises DNA chains having a thiol end group.

3. The process of claim 1, wherein the particles are spheres having an average diameter of 50 nm to 100 µm.

4. The process of claim 1, further comprising the step of, prior to attaching the functionalizing agent, treating the particles to remove a portion of the first material.

5. The process of claim 4, wherein the first material is formed by a physical vapor deposition technique, and wherein the treating step is performed by wet etching the first material.

6. The process of claim 5, wherein the particles are spheres.

7. The process of claim 4, wherein the first material comprises gold.

8. The process of claim 4, further comprising the step of, prior to treating the particles, stamping a second material onto a portion of the deposited first material.

9. The process of claim 4, further comprising the steps of:
    attracting the functionalizing agent of the functionalized particles onto the surface of a substrate to form a layer of the functionalized particles;
    forming a removable layer over the layer of particles such that non-functionalized portions of the particles are exposed above the removable layer;
    forming a second material on at least part of the non-functionalized exposed portions of the particles, wherein the second material is the same as or different from the first material;
    attaching a second functionalizing agent to the second material, wherein the second functionalizing agent is the same as or different from the first material; and
    removing the removable layer before or after attaching the second functionalizing agent.

10. The process of claim 1, further comprising the steps of:
    prior to depositing the first material, forming a removable layer over the layer of particles such that portions of the particles are exposed above the removable layer, wherein the first material is deposited on at least part of the exposed portions; and
    removing the removable layer before or after attaching the functionalizing agent.

11. The process of claim 10, wherein the first material is formed by a physical vapor deposition technique.

12. The process of claim 10, wherein the first material comprises gold.

13. The process of claim 12, wherein the functionalizing agent comprises a single strand DNA having a thiol end group.

14. The process of claim 10, wherein the particles are spheres.

15. The process of claim 10, wherein forming the removable layer comprises the steps of:
   forming an initial removable layer such that the particles are completely covered by the initial removable layer; and
   etching the top region of the initial removable layer to form the removable layer.

16. The process of claim 10, further comprising the steps of:
   attracting the functionalizing agent of the functionalized particles onto the surface of a substrate to form a layer of the functionalized particles;
   forming a second removable layer over the layer of particles such that non-functionalized portions of the particles are exposed above the removable layer;
   forming a second material on at least part of the non-functionalized exposed portions of the particles, wherein the second material is the same as or different from the first material;
   attaching a second functionalizing agent to the second material, wherein the second functionalizing agent is the same as or different from the first functionalizing agent; and
   removing the removable layer before or after attaching the second functionalizing agent.

17. The process of claim 1 wherein the layer is a monolayer that covers 5–90% of the substrate surface.

18. A process for fabricating functionalized particles, comprising the steps of:
   forming a layer of particles on a substrate;
   forming a removable layer over the layer of particles, such that portions of the particles are exposed above the removable layer;
   attaching a functionalizing agent to at least part of the exposed portions of the particles; and
   removing the removable layer.

19. The process of claim 18, wherein the particles have an average effective diameter of 50 nm to 100 µm.

20. The process of claim 18, wherein forming the removable layer comprises the steps of:
   forming an initial removable layer such that the particles are completely covered by the initial removable layer; and
   etching the top region of the initial removable layer to form the removable layer.

21. The process of claim 18, wherein the particles comprise silica and the functionalizing agent comprises a silane compound.

22. The process of claim 21, wherein the silane compound exhibits a polar structure.

23. The process of claim 18, further comprising the steps of:
   attracting the functionalizing agent of the functionalized particles onto the surface of a substrate to form a layer of the functionalized particles;
   forming a second removable layer over the layer of particles such that non-functionalized portions of the particles are exposed above the removable layer;
   attaching a second functionalizing agent to the non-functionalized portions, wherein the second functionalizing agent is the same as or different from the first material; and
   removing the second removable layer before or after attaching the second functionalizing agent.

24. An article having a periodic structure of functionalized particles comprising a layer of particles on a substrate, a first material formed on a selected first portion of the particles thus forming a periodic structure with regions of first material and regions without first material, and a first functionalizing agent attached to the first material.

25. The article of claim 24, wherein the first material comprises gold and wherein the first functionalizing agent comprises DNA chains having a thiol end group.

26. The article of claim 24, wherein the particles are spheres.

27. The article of claim 26, wherein the particles comprise silica.

28. The article of claim 24, wherein the particles further comprise a second material formed on a second portion of the particle and a second functionalizing agent attached to the second material, wherein the second material is the same as or different from the first material, and wherein the second functionalizing agent is the same as or different from the first functionalizing agent.

29. The article of claim 28, wherein the particles further comprise third and fourth materials formed on third and fourth portions, respectively, of the particle, and third and fourth functionalizing agents attached to the third and fourth materials, respectively, wherein the third and fourth materials are identical or different and are the same as or different from the first and second materials, and wherein the third and fourth functionalizing agents are identical or different and are the same as or different from the first and second functionalizing agents.

* * * * *